US008057839B2

(12) United States Patent
Bovetto et al.

(10) Patent No.: US 8,057,839 B2
(45) Date of Patent: Nov. 15, 2011

(54) NANOPARTICULATED WHEY PROTEINS

(75) Inventors: Lionel Jean René Bovetto, Larringes (FR); Christophe Joseph Etienne Schmitt, Belmont S/Lausanne (CH); Martin Beaulieu, Rimouski (CA); Nicolas Carlier, Lisieux (FR); Gerlinde Unterhaslberger, Rosenheim (DE)

(73) Assignee: Nestec S.A., Vevey (CH)

( * ) Notice: Subject to any disclaimer, the term of this patent is extended or adjusted under 35 U.S.C. 154(b) by 953 days.

(21) Appl. No.: 11/691,705

(22) Filed: Mar. 27, 2007

(65) Prior Publication Data

US 2007/0231453 A1    Oct. 4, 2007

Related U.S. Application Data

(63) Continuation of application No. PCT/EP2005/010485, filed on Sep. 28, 2005.

(30) Foreign Application Priority Data

Sep. 29, 2004   (EP) ................................ 04023174

(51) Int. Cl.
```
A23J 1/00      (2006.01)
A47J 39/00     (2006.01)
A23D 7/00      (2006.01)
A23L 1/32      (2006.01)
```
(52) U.S. Cl. ........ 426/656; 426/520; 426/602; 426/614; 426/657

(58) Field of Classification Search ............. 426/656, 426/520, 614, 602, 657
See application file for complete search history.

(56) References Cited

U.S. PATENT DOCUMENTS

| | | | | |
|---|---|---|---|---|
| 4,961,953 A | * | 10/1990 | Singer et al. ................ | 426/656 |
| 4,973,488 A | | 11/1990 | Ernster ........................ | 426/580 |
| 5,188,842 A | * | 2/1993 | Visser et al. ................. | 424/535 |
| 5,750,183 A | | 5/1998 | Yamamoto et al. ........... | 426/656 |
| 6,020,017 A | * | 2/2000 | Mingione .................... | 426/590 |
| 6,051,271 A | * | 4/2000 | Yamamoto et al. ........... | 426/656 |
| 6,767,575 B1 | | 7/2004 | Huss et al. .................... | 426/656 |

FOREIGN PATENT DOCUMENTS

| | | |
|---|---|---|
| EP | 0603981 | 10/1996 |
| EP | 1 281 322 A1 | 2/2003 |
| EP | 1 314 361 A1 | 5/2003 |
| GB | 1079604 | 8/1967 |
| JP | 5500163 | 1/1993 |
| JP | 6509475 | 10/1994 |
| JP | 7099893 | 4/1995 |
| JP | 7184556 | 7/1995 |

(Continued)

OTHER PUBLICATIONS

G. Masson and R. Jost "A study of oil-in-water emulsion stabilized by whey proteins" Colloid & Polymer Sci. 264: 631-638, 1986.*

(Continued)

*Primary Examiner* — Humera Sheikh
*Assistant Examiner* — Bhaskar Mukhopadhyay
(74) *Attorney, Agent, or Firm* — Winston & Strawn LLP (57) ABSTRACT

The present invention relates to a method for producing whey proteins in nanoparticulated form and to the nanoparticulated whey proteins thus obtained. Specifically, the present invention pertains to the use of these nanoparticulated whey proteins as emulsifiers, fat substitute, micellar casein substitute, whitening, foaming, texturizing and/or filling agents.

18 Claims, 6 Drawing Sheets

FOREIGN PATENT DOCUMENTS

| | | |
|---|---|---|
| WO | WO 91/17665 | 11/1991 |
| WO | WO 93/07761 | 4/1993 |
| WO | WO 00/48473 | 8/2000 |
| WO | WO 03/011040 A1 | 2/2003 |

OTHER PUBLICATIONS

Cecilia Elofsson et al., XP002930840, "Characterization of a Cold-Gelling Whey Protein Concentrate", International Dairy Journal, vol. 7, pp. 601-608, (1997).

Jhi Young Ju et al., XP 002146903, "Gelation of pH-Aggregated Whey Protein Isolate Solution Induced by Heat, Protease, Calcium Salt, and Acidulant", Journal of Agricultural and Food Chemistry, vol. 46, No. 5, pp. 1830-1835 (1998).

J. W. Erdman, XP009039280, "The Quality of Microparticulated Protein", Journal of the American College of Nutrition, vol. 9, No. 4, pp. 398-409, (1990).

Communication Relating to the Results of the Partial International Search PCT/EP2005/010485 filed Sep. 28, 2005.

* cited by examiner

NANOPARTICULATED WHEY PROTEINS

CROSS-REFERENCE TO RELATED APPLICATIONS

This application is a continuation of International application PCT/EP2005/010485 filed Sep. 28, 2005, the entire content of which is expressly incorporated herein by reference thereto.

BACKGROUND

The present invention relates to a method for producing whey proteins in nanoparticulated form and to the nanoparticulated whey proteins thus obtained. Specifically, the present invention pertains to the use of these nanoparticulated whey proteins as emulsifiers, fat substitute, micellar casein substitute, whitening, foaming, texturizing and/or filling agents.

Fat containing food material makes up a considerable proportion of the diets of many people. One of the problems encountered with the production of such products resides in that the fat must remain stabilized over the entire shelf life of the product, so that no phase separation occurs.

To this end, emulsifying agents are utilized, that provide a stabilization of the emulsion once formed, based on their inherent property of a lipophilic or hydrophobic part; respectively; being soluble in the non-aqueous phase and a polar or hydrophilic part being soluble in water such that said molecules are facilitate emulsifying one phase in the other phase. Additionally, the emulsifying agents also protect the once formed droplets from aggregation and coalescence. As emulsifying agents naturally occurring substances are used, such as hydrocolloids, phospholipids (lecithin) or glycolipids and on the other hand synthetic agents like stearyl-2-lactylate or mono-, diacylglycerides, etc.

One of the major drawbacks of the agents resides in that these agents sometimes substantially add to the costs of the final product, and do not add to the nutritional value of the product. Sometimes, such kinds of materials also do not show adequate stabilizing properties because of an interfacial competition with proteins. This, there is a need for alternatives to existing emulsifiers that do not show the inherent disadvantages and are readily available. The present invention now satisfies this need.

SUMMARY OF THE INVENTION

The present invention now provides a fat substitute, whitening, foaming, texturizing and/or filling agent that has a high Protein Efficiency Ratio (PER) and a method for forming it.

A method for the production of nanoparticulated whey protein is proposed that comprises the step of subjecting a solution containing whey proteins to a specific temperature for a specific period of time and in a narrow pH range to result in the production of whey protein aggregates having a diameter of less than 1 μm, preferably from 100 to 990 nm. In particular, the present invention relates to a method for the production of nanoparticulated whey protein comprising the steps of adjusting the pH at a narrow range of an aqueous solution of whey protein, or adjusting the ionic strength of the whey protein preparation while keeping the pH constant, and subjecting the aqueous solution to a temperature of between 80° C. to 95° C., during a time period of from 10 seconds to 30 minutes, to obtain a liquid dispersion of spherical nanoparticulated whey protein having a particle size of less than 1 μm.

The nanoparticulated whey protein dispersion may be further dried, in particular by freeze-drying or spray-drying. It has been found that whey protein nanoparticles were observed in solution after reconstitution of the spray-dried powder. No difference of morphology and structure could be detected, confirming that whey protein nanoparticles are physically stable regarding spray drying. These nanoparticles, which were found to have a Protein Efficiency Ratio of at least 100, also represent another embodiment of the invention.

DETAILED DESCRIPTION OF THE PREFERRED EMBODIMENTS

During extensive experiments leading to the present invention, it was surprisingly found noted that when adjusting the pH at a very precise narrow range (precise meaning ±0.2 pH units) before heat treating an aqueous solution of whey proteins or one or more of its major constituents at a temperature of between about 80° C. to 95° C., for a time period of between about 10 s to 30 min at the desired temperature, the whey proteins thus obtained show a particulate form with spherical shape and a particle size having diameters of less than 1 μm. An unexpected advantage of this form is that the whey protein particles have not been submitted to any mechanical stresses which would lead to a reduction of particle size, contrary to conventional processes. The method of the present invention induces spontaneous nanoparticulation of whey proteins during heat treatment in absence of shearing to obtain these improved nanoparticles.

The nanoparticulated whey proteins have shown to be ideally suited for use as an emulsifiers, fat substitutes, substitutes for micellar casein or foaming agents, since they are able to stabilize fat and/or air in an aqueous system for a prolonged period. In addition, the present nanoparticulated whey proteins are still in a condition that enables them to serve as whitening agents, so that with one product several tasks may be fulfilled. Since whey is a material that is abundantly available, its use reduces the cost of a product that is used as an emulsifying, filling, whitening or foaming agent, while at the same time whey adds to the nutritional value of the product. This combination of features renders the products of the invention highly desirable for use as such agents compared to conventional materials or products.

Any commercially available whey protein isolates or concentrates may be used as the whey protein to be used in the present method and product. For example, whey protein obtained by any process for the preparation of whey protein known in the art, as well as whey protein fractions prepared there from or proteins such as β-lactoglobulin (BLG), α-lactalbumin and serum albumin are suitable. In particular, sweet whey obtained as a by-product in cheese manufacture, and acid whey as by-product in acid casein manufacture, native whey obtained by milk microfiltration or rennet whey as by-product in rennet casein manufacture may be used as the whey protein. Preferably, an in particular when low cost is required or necessary, a whey protein preparation which has not been subjected to additional fractionation processes after its production, is preferred as starting material. The present invention is not restricted to whey isolates from bovine origin, but pertains to whey isolates from all mammalian animal species, such as from sheep, goats, horses, and camels. Also, the process according to the present invention also applies to any other demineralized or slightly mineralized globular protein, such as egg protein, soy, cereals, oilseeds, or from other vegetables or animal origin. It should be understood that the term "slightly mineralized" is meant to include a process that eliminates free minerals which are dialyzable or diafiltrable, while maintaining minerals associated to protein or natural mineralization after preparation of whey protein concentrate or isolate without specific mineral enrichment.

The whey proteins are present in aqueous solution in an amount of 0.1 wt.-% to 12 wt.-%, preferably in an amount of 0.1 wt.-% to 8 wt.-%, more preferably in an amount of 0.2 wt.-% to 7 wt.-%, even more preferably in an amount of 0.5 wt.-% to 6 wt.-%, in particular in an amount of 1 wt.-% to 4 wt.-%, each on the basis of the total weight of the solution.

The aqueous solution of the whey protein preparation as present before nanoparticulation step may also comprise additional compounds, such as by-products of the respective whey production processes, other proteins, gums or carbohydrates. The solution may also contain other food ingredients (fat, carbohydrates, plant extracts, etc). The amount of such additional compounds should not exceed 50 wt.-%, preferably 20 wt.-%, and more preferably 10 wt.-% of the total weight of the solution.

Whey proteins have a better protein efficiency ratio (PER) compared for example to casein 118/100. PER=body weight growth (g)/protein weight intake (g).

| Examples: | PER | % Casein |
|---|---|---|
| casein | 3.2 | 100 |
| Egg | 3.8 | 118 |
| Whey | 3.8 | 118 |
| Whole Soya | 2.5 | 78 |
| Wheat gluten | 0.3 | 9 |

Whey proteins are an excellent source of essential amino acids (AA) (45%). Rich in AA which requirements may be increased in case of stress and in elderly: compared to casein (0.3 g cysteine/100 g protein) sweet whey proteins contain 7 times more cysteine and acid whey 10 times more cysteine. Cysteine is the rate limiting amino acid for glutathione (GSH) synthesis, glutathione is a tripeptide made of glutamate cysteine and glycine. Glutathione has primary important functions in the defense of the body in case of stress. Oral supplementation with whey protein increases plasma GSH levels of HIV-infected patients (Eur. J. Clin. Invest. 2001; 31, 171-178)

The whey protein nanoparticles of the present invention have a PER of at least 100, preferably at least 118.

The whey proteins, as well as the fractions and/or the main proteins thereof may be used in purified form or likewise in form of a crude product. According to a preferred embodiment, the salt content of the starting material for the preparation of the nanoparticulated whey protein may be less than 2.5% in divalent cations, more preferably less than 2%.

Alternatively, if no pH adjustment step is desired, it is possible to adjust the ionic strength of the whey protein preparation while keeping the pH constant. Then, ionic strength may be adjusted by organic or inorganic ions in such a way that is allows nanoparticulation at constant pH.

The starting material is then subjected to the heat treatment. In this respect it has been found important for obtaining nanoparticulated whey protein to have the temperature in the range of from about 80° C. to about 95° C., preferably of from about 82° C. to about 89° C., more preferably of from about 84° C. to about 87° C., most preferred at about 85° C.

Once the desired temperature has been reached, it should be maintained for a minimum of 10 seconds and a maximum of 30 minutes (at the desired temperature). Preferably the time period, during which the aqueous whey protein solution is kept at the desired temperature ranges of from 12 to 25 minutes, more preferably from 12 to 20 minutes, or even more preferably about 15 minutes.

By nanoparticles, in the present description, what is meant is particles having a diameter of less than 1 μm, preferably between 100 and 700 μnm. The mean diameter of the nanoparticles can be determined using Transmission Electron Microscopy (TEM). In this case, the liquid nanoparticulated samples were encapsulated in agar gel tubes. Fixation was achieved by immersion in a solution of 2.5% glutaraldehyde in 0.1M, pH 7.4 cacodylate buffer and post-fixation with 2% Osmium tetroxide in the same buffer, both solutions containing 0.04% Ruthenium red. After dehydration in a graded ethanol series (70, 80, 90, 96, 100% ethanol), the samples were embedded in Spurr resin (Spurr/ethanol 1:1, 2:1, 100%). After polymerization of the resin (70° C., 48 hours), semi-thin and ultra-thin sections were cut with a Leica ultracut UCT ultra-microtome. Ultra-thin sections, stained with aqueous uranyl-acetate and lead citrate, were examined in transmission electron microscopy (Philips CM12, 80 kV).

According to the present invention, the pH and the ionic strength were found to be important factors of the method. Thus, for extensively dialyzed samples which are virtually devoid of or depleted in free cations like Ca, K, Na, Mg, it has been found that when performing the heat treatment during the time period indicated at a pH below 5.4, curd would be obtained, while at a pH exceeding 6.8, soluble whey protein will result. Thus, only in this rather narrow pH window whey protein in the particulate form with a size having a diameter of less than 1 μm will be obtained. The same particulate form is obtained symetrically below the isoelectrical pH, i.e., from 3.5 to 5.

According to a preferred embodiment, to obtain negatively charged nanoparticles, the pH is adjusted in a range of from 5.6 to 6.4, more preferably from 5.8 to 6 for a low content (below 0.2 g for 100 g of in initial whey protein powder) of divalent cations. The pH may be increased up to 8.4 depending on mineral content of whey protein source (concentrate or isolate). In particular, the pH may be between 7.5 to 8.4, preferably 7.6 to 8 to obtain negatively charged nanoparticles in presence of large amount of free minerals and the pH may be between 6.4 to 7.4, preferably 6.6 to 7.2 to obtain negatively charged nanoparticles in presence of moderate content of free minerals. The pH is generally adjusted by the addition of acid, which is preferably food grade, such as e.g. hydrochloric acid, phosphoric acid, acetic acid, citric acid, gluconic acid or lactic acid. When mineral content is high the pH is generally adjusted by the addition of alkaline solution, which is preferably food grade, such as sodium hydroxide, potassium hydroxide or ammonium hydroxide.

According to another preferred embodiment, to obtain positively charged nanoparticles, nanoparticulation of whey proteins is done in a salt free solution at pH adjusted between 3.5 and 5 depending on mineral content of protein source.

According to yet another preferred embodiment, the pH can be adjusted in the range of from 6.3 to 9 for a content of divalent cations comprised between 0.2% and 2.5% in whey protein powder.

If desired, a buffer may be added to the aqueous solution of whey protein so as to avoid a substantial change of the pH value during heat treatment of the whey protein. In principle, the buffer may be selected from any food-grade buffer system, i.e., acetic acid and its salts, such as e.g. sodium acetate or potassium acetate, phosphoric acid and its salts thereof, e.g. $NaH_2PO_4$, $Na_2HPO_4$, $KH_2PO_4$, $K_2HPO_4$, or citric acid and its salts etc.

The nanoparticulated whey proteins obtained according to the present method typically have a size with a diameter of less than 1 µm, preferably of from 100 to 990 nm, more preferably from 100 to 700 nm, while depending on desired application the proportion of nanoparticles is of at least 80% and residual soluble aggregates or soluble protein below 20%. The average nanoparticle size is characterized by a polydispersity index below 0.2. In consequence, the white suspension obtained by the present invention is stable and has a milky appearance in a large range of pH 3 to 8.

The turbidity measured by absorbance at 500 nm is at least 3 absorbance units for 1% protein solution but can reach 16 absorbance units when the yield of nanoparticulation is above 80%.

The purity of nanoparticulated whey proteins produced according to the method of the present invention can be obtained by determining the amount of residual soluble proteins. Nanoparticles are eliminated by centrifugation at 20° C. and 26900 g for 15 min. The supernatant is used to determine the protein amount in quartz cuvettes at 280 nm. Values are expressed as a percentage of the initial value before heat treatment.

Proportion of nanoparticles=(Amount of initial proteins−amount of soluble proteins)/Amount of initial proteins Without wishing to be bound by any theory it is presently believed that the method as described results in the formation of very small aggregates of whey proteins, i.e., aggregates having the size indicated, and being in a particular denatured status resulting from an electrostatic balance between repulsive and attractive forces present at the surface of the proteins, that produces the properties observed. In particular, since the nanoparticulated whey proteins have perfect emulsifying and foaming properties, the denatured status of the protein seems to allow interaction with a hydrophobic phase, e.g., a fat droplet or air, and a hydrophilic phase, the aqueous solution.

Thus, according to another embodiment, the present invention also relates to the use of the nanoparticulated whey proteins as an emulsifying agent, for which the material is ideally suited, since it has a neutral taste, i.e., no off-flavor is created by the use of such material. They may also be used as micellar casein substitute.

The nanoparticulated whey proteins obtained according to the method of the present invention can be used for the preparation of any kind of food product requiring stabilization of an emulsion or a foam, such as e.g., present in mousse or ice cream, in coffee creamers, or also in low fat or essentially fat free dairy products, or also where it finds application, as a micellar casein substitute. Examples for products, where the present nanoparticulated whey proteins may find application are exemplarily, pasteurized UHT milk, sweet condensed milk, yoghurt, fermented milks, milk-based fermented products, milk chocolate, mousses, foams, emulsions, ice creams, fermented cereal based products, milk based powders, infant formula, diet fortifications, pet food, tablets, liquid bacterial suspensions, dried oral supplement, wet oral supplement.

In particular, the present nanoparticulated whey proteins may be used either alone or together with other active materials, such as polysaccharides (e.g. acacia gum or carrageenans) to stabilize matrices and for example milky foam matrices. Due to their neutral taste, whitening power and stability subsequent to heat treatment, the present nanoparticulated whey proteins may be used to increase skimmed milk whiteness and mouthfeel.

Apart from increasing the whitening power of dairy systems for the same total protein content, at the same time the fat content in a food matrix may be reduced. This feature represents a particular advantage of the present nanoparticulated whey proteins, since it allows e.g. adding a milk creamer without adding additional fat derived from the milk as such.

Hence, according to another embodiment the present invention also encompasses a food product, a food supplement, a nutritional and/or pharmaceutical composition containing nanoparticulated whey proteins as described herein.

EXAMPLES

The invention is further defined by reference to the following examples describing in detail the preparation of the nanoparticles of the present invention. The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Example 1

Nanoparticulation of β-Lactoglobulin

β-Lactoglobulin (lot JE002-8-922, 13-12-2000) was obtained from Davisco (Le Sueur, Minn., USA). The protein was purified from sweet whey by ultra-filtration and ion exchange chromatography. The composition of the powder is 89.7% protein, 8.85% moisture, 1.36% ash (0.079% $Ca^{2+}$, 0.013% $Mg^{2+}$, 0.097% $K^+$, 0.576% $Na^+$, 0.050% $Cl^-$). All other reagents used were of analytical grade (Merck Darmstadt, Germany).

The protein solution was prepared at 0.2% concentration by solvation of β-lactoglobulin in MILLIQ® water (Millipore), and stirring at 20° C. for 2 h. Then pH of aliquots was adjusted to 5.0, 5.2, 5.4, 5.6, 5.8, 6.0, 6.2, 6.4, 6.6, 6.8, 7.0 by HCl addition. The solutions were filled in 20 ml glass vials (Agilent Technologies) and sealed with aluminum capsules containing a silicon/PTFE sealing. The solutions were heated at 85° C. for 15 min (time to reach the temperature 2.30 to 3.0 min). After the heat treatment, the samples were cooled in ice water to 20° C.

Figure 1:
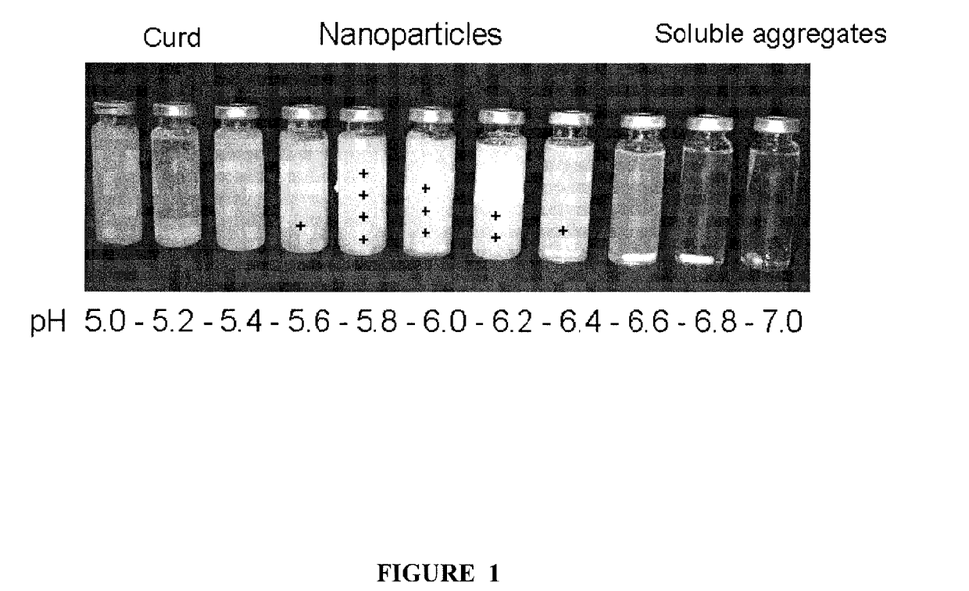
FIG. 1 shows the result of an experiment demonstrating the effect of pH and heat treatment on the nanoparticulation of β-lactoglobulin.

The visual aspect of products (FIG. 1) indicates that the optimal pH of nanoparticulation is 5.8.

Example 2

Nanoparticulation of Whey Protein Isolate

Whey protein isolate (WPI) (BIPRO®, Batch JE032-1-420) was obtained from Davisco (Le Sueur, Minn., USA). The composition of the powder is reported in Table 1.

The protein solution was prepared at 3.4% protein by solvation of whey protein powder in MILLIQ® water (Millipore), and stirring at 20° C. for 2 h. The initial pH was 7.2. Then pH of aliquots was adjusted at 5.6, 5.8, 6.0, 6.2, 6.4 and 6.6 by HCl 0.1N addition.

The solutions were filled in 20 ml glass vials (Agilent Technologies) and sealed with aluminum capsules containing a silicon/PTFE sealing. The solutions were heated at 85° C. for 15 min (time to reach the temperature 2.30 to 2.50 min). After the heat treatment, samples were cooled in ice water to 20° C.

The turbidity of heated whey proteins has been determined at 500 nm and 25° C., samples were diluted to allow the measurement in the range of 0.1-3 Abs unit (Spectrophotometer Uvikon 810, Kontron Instrument). Values were calculated for the initial protein concentration 3.4%.

Figure 2:
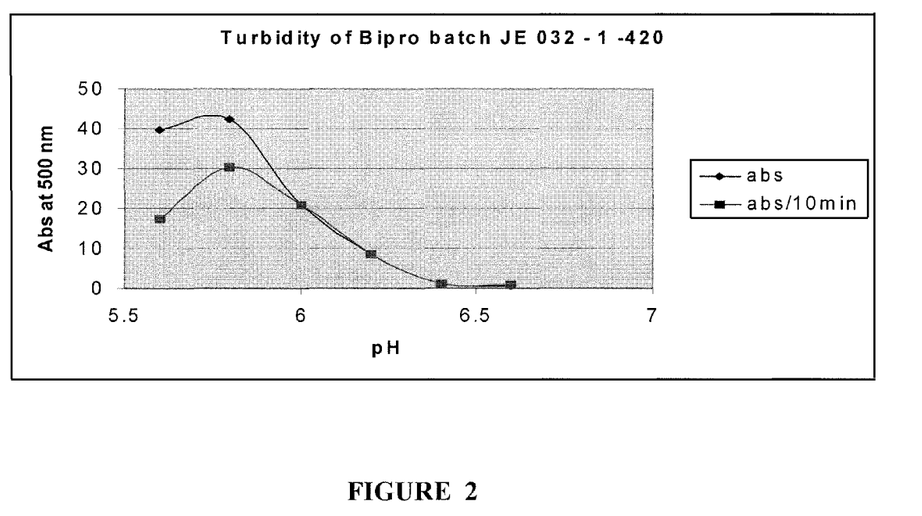
FIG. 2 is showing a mean to determinate the pH of nanoparticulation for a commercial preparation (BIPRO®, Batch JE032-1-420) using turbidity measurements at 500 nm.

The pH of nanoparticulation was considered to be reached upon stability (less than 5% variation of the initial value) of the absorbance measured at 500 nm within an interval of 10 minutes for the same sample as illustrated by the FIG. 2. For this product the optimal pH for nanoparticulation was 6.0 to 6.2. For this pH adjusted before heat treatment stable turbidity was 21 and residual soluble protein evaluated by absorbance at 280 nm after centrifugation was 1.9%. We can conclude that 45% of initial proteins were transformed in nanoparticles at pH 6.0.

TABLE 1

Composition of WPI and sample characteristics after nanoparticulation

| | |
|---|---|
| Supplier | Davisco |
| Product name | BIPRO ® |
| Batch number | JE 032-1-420 |
| Composition (mg/100 g) | |
| Sodium | 650 |
| Potassium | 44 |
| Chloride* 10 if ≦40 | 10 |
| Calcium | 82 |
| Phosphorus | 49 |
| Magnesium | 6 |
| Initial pH | 7.2 |
| pH nanoparticulation | 6.0 |
| Turbidity (500 nm) for 3.4% protein in solution | 21 |
| Residual Soluble protein (%) by absorbance at 280 nm | 1.9 |

Example 3

Microscopic Observation of Nanoparticles

Production of Nanoparticles:

Protein solution was prepared at 2% protein by solvation of whey protein powder (WPI 90 batch 989/2, Lactalis, Retier, France) in MILLIQ® water (Millipore), and stirred at 20° C. for 2 h. Then pHs of aliquots were adjusted using HCl 0.1N or NaOH 0.1N.

The solutions were filled in 20 ml glass vials (Agilent Technologies) and sealed with aluminum capsules containing a silicon/PTFE sealing. The solutions were heated at 85° C. for 15 min (time to reach the temperature 2.30 to 2.50 min). After the heat treatment, the samples were cooled in ice water to 20° C. For this product the optimal pH for nanoparticulation was 7.4.

Microscopic Observations:

Liquid nanoparticulated samples were encapsulated in agar gel tubes. Fixation was achieved by immersion in a solution of 2.5% glutaraldehyde in 0.1M, pH 7.4 cacodylate buffer and post-fixation with 2% Osmium tetroxide in the same buffer, both solutions containing 0.04% Ruthenium red. After dehydration in a graded ethanol series (70, 80, 90, 96, 100% ethanol), the samples were embedded in Spurr resin (Spurr/ethanol 1:1, 2:1, 100%). After polymerization of the resin (70° C., 48 hours), semi-thin and ultra-thin sections were cut with a Leica ultracut UCT ultra-microtome. Ultra-thin sections, stained with aqueous uranyl-acetate and lead citrate, were examined in transmission electron microscopy (Philips CM12, 80 kV).

Figure 3:
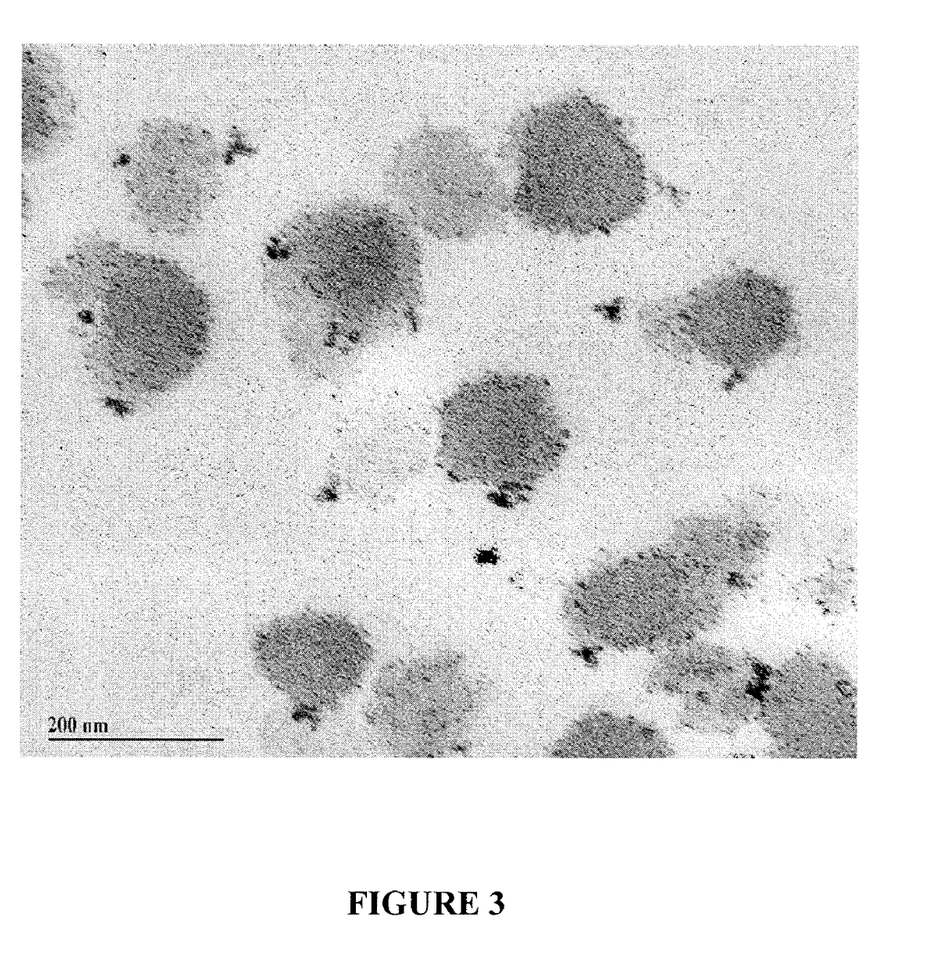
FIG. 3 is a Transmission Electron Microscopy micrograph from nanoparticulated whey proteins (2 wt.-%, WPI 95, Lactalis) at pH 7.4. Scale bar is 200 nm.

TEM micrograph is presented in FIG. 3. Obtained nanoparticles are presenting a spherical shape with a diameter of 200 nm.

Particle Size Distribution

Figure 6:
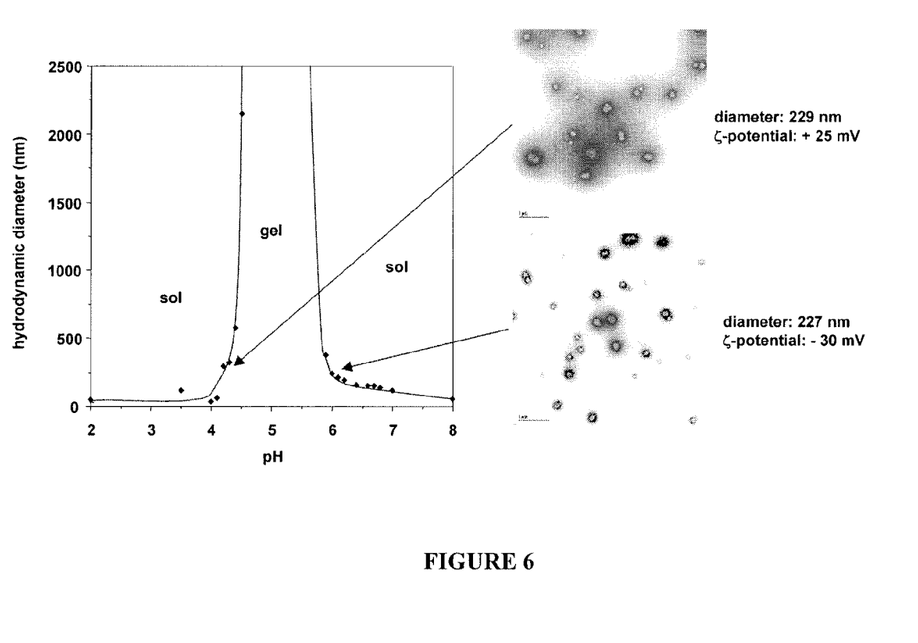
FIG. 6 shows the intensity-based size distribution of nanoparticles obtained by heat-treatment of a 1 wt % β-lactoglobulin dispersion for 15 min at 85° C. at pH 4.25 (positively charged with a zeta potential around +25 mV) and at pH 6.0 (negatively charged with a zeta potential around −30 mV). Z-averaged hydrodynamic diameter of the nanoparticles was 229.3 mm at pH 4.25 an 227.2 at pH 6.0. The corresponding micrographs of the nanoparticles obtained by TEM after negative staining are shown. Scale bars are 1 μm.

The intensity-based size distributions of nanoparticles were measured for nanoparticles obtained by heat-treatment of a 1 wt % β-lactoglobulin dispersion for 15 min at 85° C. at pH 4.25 (positively charged with a zeta potential around +25 mV) and at pH 6.0 (negatively charged with a zeta potential around −30 mV). Z-averaged hydrodynamic diameter of the nanoparticles was 229.3 mm at pH 4.25 and 227.2 at pH 6.0. β-LG and whey protein aggregations were followed using dynamic light scattering. A Nanosizer ZS apparatus (Malvern Instruments, UK) equipped with a laser emitting at 633 nm and with 4.0 mW power was used. The instrument was used in the backscattering configuration, where detection is done at a scattering angle of 173°. This allows considerable reduction of the multiple scattering signals found in turbid samples. Samples were placed in a squared quartz cell (Hellma, pathlength 1 cm). The pathlength of the light beam was automatically set by the apparatus, depending on the sample turbidity (attenuation). The autocorrelation function was calculated from the fluctuation of the scattered intensity). The results are presented in FIG. 6. It shows that the average particle is characterized by a very narrow polydispersity index (<0.200). In consequence, the white suspension obtained by the present invention is stable and has a milky appearance in a large range of pH 3-8.

Example 4

Nanoparticulation of a β-Lactoglobulin at a Constant pH

The method described in Example 1 was repeated with the proviso of using an aqueous solution of 2% β-lactoglobulin. The pH of this solution has been adjusted to 7.0 after adding Arginine HCl solutions to obtain a final salt concentration ranging from 5 to 200 mM and a final β-lactoglobulin concentration of 1%. Subsequent heat treatment (80° C., 10 min, about 2 min heating up) was carried out to produce nanoparticles.

Figure 4:
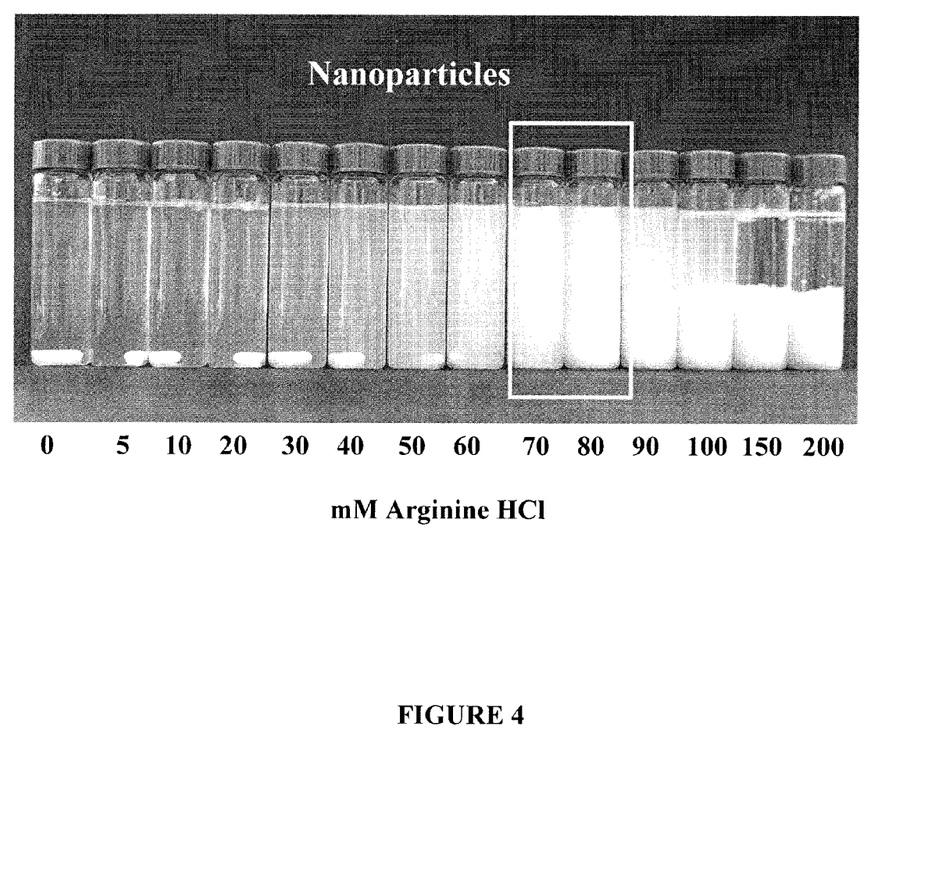
FIG. 4 shows the result of an experiment evaluating the impact of the ionic strength (Arginine HCl) on the formation of protein nanoparticles at constant pH of 7.0.

The results are shown in FIG. 4 and clearly indicate that only in the ionic strength range of from about 50 to 70 mM a substantial turbidity, indicating the presence of nanoparticulated whey proteins, has been observed.

Example 5

Preparing a Whitening Agent

Native whey proteins (WPI 95 batch 848, Lactalis; 8 wt-% aqueous solution) were treated according to Example 2. The resulting product lightness (L) was measured in trans-reflectance mode using a MacBeth CE-XTH D65 10° SCE apparatus equipped with a 2 mm measuring cell. The resulting lightness was L=74.8, that could be compared to the value of L=74.5 for full-fat milk.

Example 6

Preparing a Coffee Creamer

Native whey proteins (BIPRO®, lot JE 032-1-420, 0.5 wt-% aqueous solution) were mixed at 50° C. with 10 wt.-% partially hydrogenated palm oil, 14 wt.-% maltodextrin (DE 21) and in presence of 50 mM phosphate-citrate buffer adjusted to the nanoparticulation pH of 6.0 for this BIPRO®. The mixture was homogenized under 400/50 bars using a Rannie homogenizer and subsequently heat-treated for 15 minutes at 85° C.

The emulsion obtained showed a high stability over a time period of at least one month at the conditions of storage at 4° C. and gave a whiteness of L=78 compared to a reference liquid creamer (Crème à Café, Emmi, Switzerland) having a fat content of 15% and a lightness of L=75.9.

Example 7

Preparing an Aqueous Foam

Figure 5:
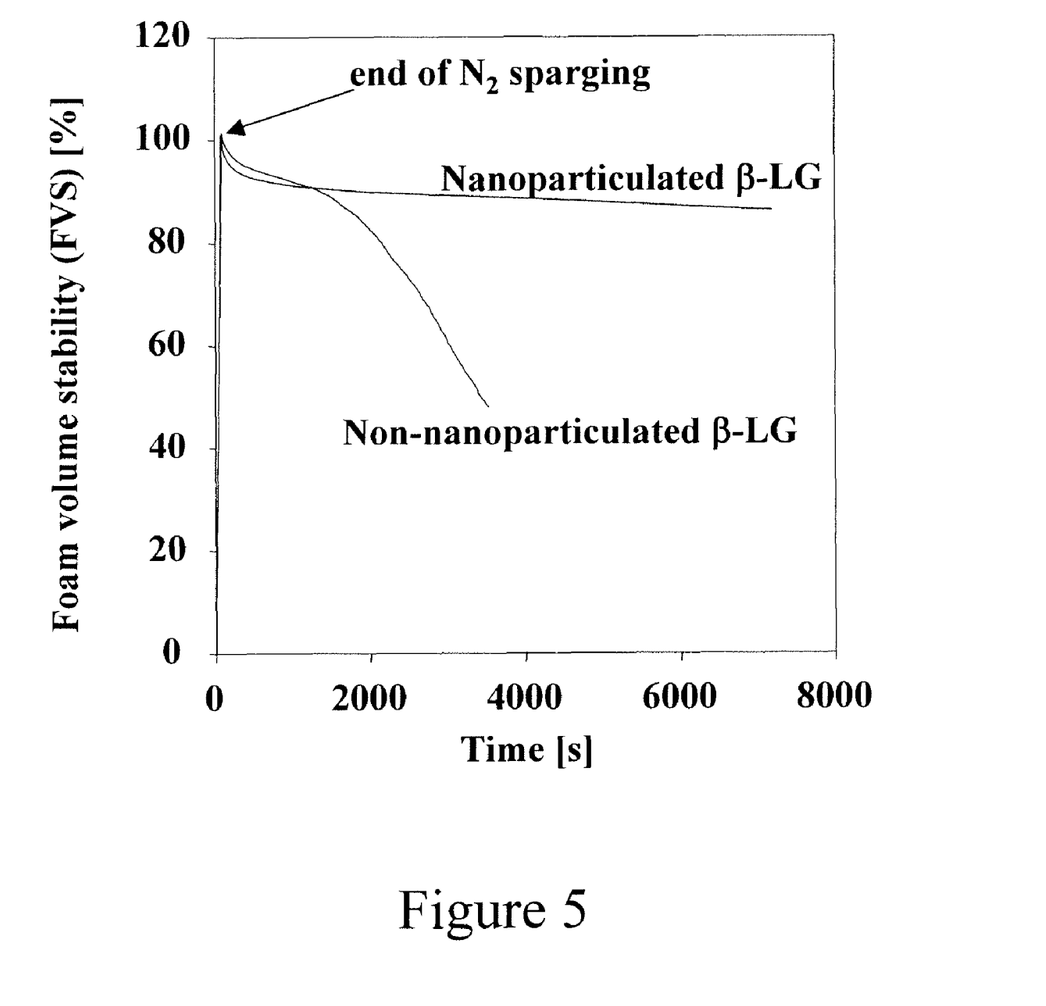
FIG. 5 shows the volume stability (FVS) of foam stabilized by 1 wt.-% β-lactoglobulin nanoparticles (Davisco) at pH 7.0 in presence of 60 mM Arginine HCl compared to non-nanoparticulated β-lactoglobulin.

Native β-lactoglobulin (Biopure, Davisco, lot JE 002-8-922, 2 wt-% aqueous solution) was mixed with 120 mM Arginine HCl solution so that the final β-lactoglobulin concentration was 1 wt.-% and Arginine HCl 60 mM. The pH was then adjusted to 7.0 by addition of 1N HCl. The mixture was then heat treated at 80° C. for 10 minutes so that 90% of initial β-lactoglobulin was converted into nanoparticles having a z-averaged diameter of 130 nm. In this case, the diameter of the nanoparticles was determined using a Nanosizer ZS apparatus (Malvern Instruments, UK). The sample was poured in a quartz cuvette and variations of the scattered light were recorded automatically. The obtained autocorrelation function was fitted using the cumulants method so that the diffusion coefficient of the particles could be calculated and thereafter the z-averaged hydrodynamic diameter using the Stokes-Einstein law. For this measurement, the refractive index of the solvent was taken as 1.33 and that of the nanoparticles 1.45. A volume of 50 mL of the resulting dispersion of β-lactoglobulin nanoparticles is then foamed by nitrogen sparging through a glass frit generating bubbles of 12-16 μm to produce a foam volume of 180 cm³ using the standardized Foamscan™ (ITConcept) apparatus. The volume stability of the foam was then followed with time at 26° C. using image analysis and compared to the stability of the foam obtained with β-lactoglobulin treated in the same conditions, but without Arginine HCl, where no nanoparticles were formed. FIG. 5 shows that the foam volume stability is greatly improved by the presence of β-lactoglobulin nanoparticles.

Example 8

Whey Based Fermented Dairy Product—Fermentation Trials

Material
Whey protein isolate (WPI) (BIPRO®) was obtained from Davisco (Le Sueur, Minn., USA) (protein concentration 92.7%).
Spray dried whey permeate (Variolac 836): Lactose concentration: 83%-Minerals: 8%
Lactic Acid 50%
Edible Lactose (Lactalis)
De-ionized water
Method
The BIPRO® powder was dissolved in de-ionized water in order to have a protein concentration of 4.6%, i.e. for 3 liters of solution 154.5 g of WPI powder and 2845.5 g of water. The hydration time was 3 hours. After hydration, this solution has been divided in samples of 200 ml to prepare the different trials:

TABLE 2

| Trial | Whey permeate (%) | Lactose (%) | pH adjustment | Heating 85° C./ 15 min |
|---|---|---|---|---|
| 1 | 2.9 | 2.5 | 6.5 | + |
| 2 | 0 | 5 | 6 | + |
| 3 | 0 | 5 | 6.7 | − |
| 4 | 0 | 5 | 6.7 | + |
| 5 | 0 | 5 | 6.1 | + |
| 6 | 0 | 0 | 6 | + |
| 7 | 0 | 5 (added after pH adjustment) | 6 | − |
| 8 | 0 | 5 (added after pH adjustment) | 6 | + |

For each solution, lactic acid at 50% has been added to adjust the pH before heating. Samples were heated with the double boiler up to 85° C. and maintain at this temperature during 15 minutes. After heating, solutions were cooled at 40° C. and inoculated with *Lactobacillus bulgaricus* and *Streptococcus thermophilus*. Samples stayed 5 h 30 in a steam room at 41° C. before in a cold room at 6° C. The results are presented in Table 3.

TABLE 3

| Trial | Whey permeate | Lactose | pH | Heating | pH after 5 h 30 | Aspect |
|---|---|---|---|---|---|---|
| 1 | + | + | 6.5 | + | 4.68 | Very firm |
| 2 | − | + | 6 | + | 4.7 | Firm |
| 3 | − | + | 6.7 | − | 5.78 | Liquid |
| 4 | − | + | 6.7 | + | 4.81 | Very firm |
| 5 | − | + | 6.1 | + | 4.59 | Very firm |
| 6 | − | − | 6 | + | 4.99 | Very firm |
| 7 | − | − added after pH adjustment | 6 | − | 4.87 | Liquid with white speckles |
| 8 | − | − added after pH adjustment | 6 | + | 4.77 | Firm |

Example 9

Whey Protein Boosted Ice Cream with Reduced Fat Content

Material
Whey protein isolate (WPI, PROLACTA90® from Lactalis, Rétiers, France) with a protein content of 90%
Skim milk powder with 35% protein content Sucrose
Maltodextrins DE39
Anhydrous milk fat
Emulsifier
De-ionized water
Edible hydrochloric acid 1M
Method Using a double-jacketed 80 L tank, the PROLACTA90® powder was dispersed at 50° C. in de-ionized water at a protein concentration of 9.67 wt % under gentle stirring in order to avoid foam formation, i.e. 3.3 kg of Prolacta90® were dispersed in 31.05 kg of de-ionized water. After 1 hour of dispersion, the pH of the dispersion was adjusted to the nanoparticulation pH by addition of HCl. The temperature of the dispersion was raised to 85° C. and maintained for 15 minutes in order to generate the whey protein nanoparticles. After 15 minutes, the temperature was decreased to 50° C. and the additional ingredients were sequentially added to the nanoparticles dispersion (i.e. skim milk powder, maltodextrins DE39, sucrose, emulsifier and anhydrous milk fat). The final amount of mix was 50 kg with total solids content of 39.5% and a fat content of 5 wt %. After 30 minutes of hydration, the mix was two-step homogenized (80/20 bars) and pasteurized (86° C./30 s) before ageing during overnight. The day after, the ice-cream mix was frozen at an overrun of 100% using a Hoyer MF50 apparatus and hardened at −40° C. before storage at −20° C. The final ice cream contained 8 wt % proteins (20% caseins, 80% whey proteins) and 5 wt % fat on the ice cream mix basis.

Example 10

Powdered Whey Protein Nanoparticles Obtained by Spray Drying

Material
Whey protein isolate (WPI, PROLACTA90® from Lactalis, Rétiers, France) with a protein content of 90%
Edible lactose
Maltodextrins DE39
De-ionized water
Edible hydrochloric acid 1M
Method Using a double-jacketed 100 L tank, the PROLACTA90® powder was dispersed at 50° C. in de-ionized water at a protein concentration of 10 wt % under gentle stirring in order to avoid foam formation, i.e. 11 kg of PROLACTA90® were dispersed in 89 kg of de-ionized water. After 1 hour of dispersion, the pH of the dispersion was adjusted to the nanoparticulation pH (around 6.3 in that case) by addition of HCl. The temperature of the dispersion was raised to 85° C. and maintained for 15 minutes in order to generate the whey protein nanoparticles. After 15 minutes, the temperature was decreased to 50° C. and the 10 wt % whey protein nanoparticles dispersion was split in two batches of 50 kg. In a first trial, 20 kg of lactose were dispersed in 50 kg of nanoparticles dispersion at 50° C. and stirred for 30 min. Similarly, 20 kg of maltodextrines DE39 were added to the remaining 50 kg of whey protein nanoparticles dispersion.

The two mixtures were then spray dried into a NIRO SD6.3N tower at a flow rate of 15 L/h. The air input temperature was 140° C. and the air output temperature was 80° C. The water content of the obtained powders was lower than 5%.

The size of the whey protein nanoparticles was determined in presence of lactose and maltodextrin (DE39) in water using dynamic light scattering before and after spray drying. The total protein concentration was set to 0.4 wt % by dilution of the dispersion before spray drying or reconstitution of the powder in order to be in the dilute regime of viscosity for whey protein nanoparticles. A Nanosizer ZS apparatus (Malvern Instruments) was used and nanoparticle diameter was averaged from 20 measurements.

The particle diameter determined for whey protein nanoparticles in presence of lactose and maltodextrins (DE39) was 310.4 nm and 306.6, respectively. After reconstitution of the powders, the respective diameters were found to be 265.3 nm and 268.5, respectively. These measurements confirm than whey protein nanoparticles were physically stable regarding spray drying. The results were corroborated by TEM microscopy observations of 0.1 wt % whey protein nanoparticles dispersions in water using negative staining in presence of 1% phosphotungstic acid at pH 7. A Philips CM12 transmission electron microscope operating at 80 kV was used. Whey protein nanoparticles were observed in solution before spray drying and after reconstitution of the spray-dried powder. No difference of morphology and structure could be detected.

What is claimed is:

1. A method for the production of nanoparticulated whey protein which comprises:
    treating an aqueous solution of whey protein by adjusting the pH at a very precise narrow range of ±0.2 pH units and between 3.5 and 9 depending upon the divalent metal content of the solution or adjusting the ionic strength of the whey protein solution while keeping the pH constant, wherein (a) to obtain negatively charged particles, the treating of the aqueous whey protein solution is achieved by adjusting the pH to 5.6 to 6.4 when the divalent metal content is below 0.2 g for 100 g of initial whey protein powder or adjusting the pH to 6.3 to 9 when the divalent metal content is above 0.2 g but below 2.5 g for 100 g of initial whey protein powder; and (b) to obtain positively charged particles, the treating of the aqueous whey protein solution includes removing free cations of Ca, K, Na, and Mg and adjusting the pH to 3.5 to 5, and
    subjecting the treated aqueous whey protein solution to a heat treatment at a temperature of between about 82° C. to about 89° C. for a time period of from 12 to 25 minutes to obtain a liquid dispersion of spherical whey protein nanoparticles having a particle size of less than 1 µm;
    wherein the solution is not subjected to mechanical stresses to obtain the nanoparticles.

2. The method according to claim 1, wherein spontaneous nanoparticulation of the whey proteins is induced during heat treatment in absence of shearing, and in which the proportion of nanoparticles in the liquid dispersion is at least 20% with the proportion of residual soluble aggregates or soluble protein being below 80%.

3. The method according to claim 1, in which the average nanoparticle size is characterised by a polydispersity index below 0.2.

4. The method according to claim 1, wherein the heat treatment is conducted for a time period of 15 minutes and at a temperature of 85° C.

5. The method of claim 1, wherein the solution at a pH of 7.0 has a salt content of 5 to 200 mM.

6. The method of claim 1, which further comprises drying the dispersion of nanoparticles to form when protein nanoparticle aggregates having a size of 100 to 990 nm.

7. The method of claim 1, wherein the aqueous whey protein solution is essentially salt free or where ionic strength has been adjusted by organic or inorganic ions in such a way that is allows nanoparticulation at constant pH.

8. The method of claim 1, wherein the whey proteins are present in the aqueous solution in an amount of 0.1 wt.-% to 12 wt.-% on the basis of the total weight of the solution.

9. The method of claim 1, which further comprises adding other demineralized or slightly mineralized globular protein to the dispersion.

10. The method of claim 9, wherein the other protein is egg, soy, cereals, oilseeds, or other vegetable or animal origin protein.

11. Whey protein nanoparticles obtainable by the method of claim 1 having a Protein Efficiency Ratio of at least 100 and characterised by a particle size of 100 to 990 nm and a polydispersity index below 0.2.

12. The nanoparticles of claim 11, having a Protein Efficiency Ratio of at least 118 and a particle size of 100 to 700 nm.

13. A food product, a food supplement, a nutritional composition or a pharmaceutical composition that contains whey protein nanoparticles according to claim 11.

14. A food product according to claim 13, which is a low fat product.

15. A food product according to claim 13, in the form of a coffee creamer, yogurt, pasteurized, UHT milk, sweet condensed milk, fermented milks, a fermented milk product, milk chocolate, mousses, foams, emulsions, ice cream, milk-based powders, infant formula, diet fortifications, pet food, tablet, dried oral supplement, or wet oral supplement.

16. The method of claim 1 which further comprises adding a buffer to the solution to avoid substantial changes in pH during the heat treatment.

17. The method of claim 16 wherein the buffer is a food-grade buffer comprising acetic acid, phosphoric acid, citric acid or a salt thereof.

18. The method of claim 1 wherein the heat treatment is conducted at a temperature of from about 84° C. to about 87° C. for a time of from 12 to 20 minutes.

* * * * *